United States Patent
Dubois-Rande et al.

(10) Patent No.: US 6,468,304 B1
(45) Date of Patent: Oct. 22, 2002

(54) IMPLANTABLE DEVICE COVERED WITH POLYMER CAPABLE OF RELEASING BIOLOGICALLY ACTIVE SUBSTANCES

(75) Inventors: Jean-Luc Dubois-Rande, Créteil; Trung Le Doan, Antony; Minh Chau Pham, Bourg-la-Reine; Benoît Piro, La Rochelle; Emmanuel Teiger, Vincennes; Jean Pierre Tenu, Meudon la Forêt, all of (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/462,881

(22) PCT Filed: Jul. 15, 1998

(86) PCT No.: PCT/FR98/01538

§ 371 (c)(1),
(2), (4) Date: Mar. 20, 2000

(87) PCT Pub. No.: WO99/03517

PCT Pub. Date: Jan. 28, 1999

(30) Foreign Application Priority Data

Jul. 16, 1997 (FR) .............................. 97 09001

(51) Int. Cl.$^7$ .................................. A61F 2/06
(52) U.S. Cl. .................... 623/1.42; 604/891.1; 623/901
(58) Field of Search ............................ 606/1, 108, 194, 606/198, 195; 623/1.1, 1.11, 1.2, 1.44, 1.45, 1.46, 12, 1.42, 1.43, 1.15, 901; 604/891.1

(56) References Cited

U.S. PATENT DOCUMENTS 5,861,032 A * 1/1999 Subramanium
6,096,070 A * 8/2000 Ragheb et al.

FOREIGN PATENT DOCUMENTS

| DE | 44 29 390 A1 | 2/1996 |
|---|---|---|
| DE | 44 29 380 | 4/1996 |
| EP | 0 566 245 A1 | 10/1993 |
| EP | 0 623 354 A | 11/1994 |
| EP | 0 701 802 A | 3/1996 |
| EP | 0 701 802 A1 | 3/1996 |
| EP | 0 747 069 A | 12/1996 |
| FR | 2 724 935 | 3/1996 |
| WO | WO 96/10401 | 4/1996 |
| WO | WO 97/12899 | 4/1997 |

OTHER PUBLICATIONS

Bennett et al., J. Clin. Invest., vol. 93, Feb. 1994, 820–828.
van der Giessen et al., Circulation, 1996, vol. 94, No. 7, 1690–1697.
Delafontaine et al., J. Biol. Chem., 1995, vol. 270, No. 24, 14383–14388.
Burgess et al., Proc. Natl. Acad. Sci. USA, vol. 92, pp 4051–4055, 1995.

* cited by examiner

Primary Examiner—Michael H. Thaler
(74) Attorney, Agent, or Firm—Burns, Doane, Swecker & Mathis, L.L.P.

(57) ABSTRACT

A device which can be implanted in the body and comprises an electrically conducting support covered with a layer of electrically conducting polymer, to which layer is attached at least one biologically active substance of an anionic or cationic nature. The deposition of the polymer is carried out, in a first stage, by electropolymerization directly directly on the support or, according to an alternative form, by deposition of the polymer in solution on the support. In a second stage, electrochemical oxidation or reduction is conducted and the biologically active substance with an anionic or cationic nature is attached to the polymer.

20 Claims, No Drawings

IMPLANTABLE DEVICE COVERED WITH POLYMER CAPABLE OF RELEASING BIOLOGICALLY ACTIVE SUBSTANCES

BACKGROUND OF THE INVENTION

1. Field of the Invention

The present invention relates to an implant covered with a polymer capable of releasing various substances and, more particularly, to a stent covered with a polymer capable of encapsulating biologically active substances which are intended for the treatment of restenosis and of releasing them locally, and to a process for depositing a polymer on a support.

2. Description of the Related Art

Techniques have been developed in various medical fields which consist in introducing implants or prostheses into the human or animal body in order to correct or limit certain deficiencies.

Thus, in the field of cardiology, the technique of balloon angioplasty of arterial stenoses is widely used today in the treatment of coronary or peripheral vascular lesions responsible for angina pectoris, myocardial infarction and arteritis of the lower limbs. This technique consists in introducing, under angiographic control, a probe with an expandable balloon into the vessel to be treated at the contracted region and in reestablishing the blood flow by crushing the atheromatous plaque in the wall of the vessel. It is thus generally possible to avoid recourse to conventional surgical techniques in achieving arterial or peripheral revascularization.

However, angioplasty exhibits the disadvantage of often resulting in a further contraction of the artery, known as restenosis. In approximately 30 to 40% of cases, this restenosis occurs in a period of six months and cannot be predicted. It is essentially due to retractile healing of the artery and to proliferation of the smooth muscle cells of the arterial wall, in response to the attack produced by the introduction of the balloon. These two phenomena result in a further contraction of the arterial lumen.

The administration of medicaments, such as angiotensin converting enzyme inhibitors, anti-inflammatories, platelet anti-aggregants, anti-coagulants and the like, has not made it possible to effectively combat the phenomenon of restenosis.

Use is made, in preventing arterial retraction, of metallic endovascular prostheses in the form of a small spring, known as stents, which are inserted into the artery after having carried out the dilatation. The stent has the effect of impeding the immediate elastic return of the wall of the artery and, in the longer term, of preventing the constriction of the artery. On the other hand, the presence of the stent does not have a favorable effect on the proliferation of the smooth muscle cells and, in some cases, it can even aggravate it.

It is therefore desirable to be able to combine an effective medicinal treatment with the insertion of the stent.

It is known that some antisense oligonucleotides exert an in vitro and in vivo antiproliferative activity (M. R. Bennett et al., "Inhibition of vascular muscle cell accumulation in vitro and in vivo by c-myc antisense oligonucleotides", *J. Clin. Invest.* (1994), 93, 820–28). However, no effective technique for the administration of such compounds has been described. Antisense nucleotide derivatives adsorbed or encapsulated in poly(alkyl cyanoacrylate) nanoparticles are disclosed in Patent FR-A-2,724,935, which provides this technique for their intratumoral administration in the treatment of certain cancers.

Patent DE-A-4,429,380 discloses a process for the preparation of stents with a ceramic or metallic support which are coated with an intermediate layer of amorphous silicon and with a layer of semiconductive material, these two layers overlapping each other.

Metallic stents covered with a first composite layer of a polymer and of a therapeutically active substance coated with a second layer of fibrin are disclosed in Patent Application EP-A-701,802. The polymer used is chosen from silicones, polyurethanes, polyesters, polyethers and vinyl derivatives. Furthermore, according to Patent EP-A-566, 245, fibrin can be used in the treatment of restenosis. Tests carried out on pig coronary arteries with various biodegradable polymers (for example, polyglycolic acid/polylactic acid, polycaprolactone, and the like) or non-biodegradable polymers (polyurethane, silicone, poly(ethylene terephthalate)) have revealed significant inflammatory reactions accompanied by fibrocellular proliferation of the arterial wall (W. J. Van der Giessen et al., *Circulation,* (1996), 94, 1690–97).

Thus, there currently exists no system effectively combining, in the treatment of restenosis, a stent and a substance having an antiproliferative effect on smooth muscle cells.

SUMMARY OF THE INVENTION

A subject-matter of the present invention is therefore a device which can be implanted in the body, or endoprosthesis, and in particular a stent, covered with a polymer capable of encapsulating biologically active substances with an anionic or cationic nature and of releasing them locally, which can be used in the treatment of various conditions and in particular of endoprosthetic thrombosis and of restenosis in the field of coronary angioplasty and of peripheral arterial angioplasty.

The invention also relates to a process which makes it possible to deposit an electrically conducting polymer, comprising a biologically active substance, on an electrically conducting support, such as a metallic support and in particular a stent.

DETAILED DESCRIPTION OF THE PREFERRED EMBODIMENTS

The process in accordance with the present invention makes possible the electrochemical deposition of an electrically conducting polymer, for example a polymer derived from pyrrole, naphthalene or thiophene, which can be obtained in aqueous medium under mild conditions, that is to say at room temperature and under moderate saline conditions, from commercially available monomers. Furthermore, the electrochemical deposition makes possible precise control of the thickness of the polymer layer deposited on the support and the medium used does not comprise a chemical oxidizing agent or an organic solvent which might have harmful effects in the application envisaged. In the case where the electrochemical polymerization is difficult or cannot be envisaged, the polymer can be prepared in solution in an appropriate solvent, according to a conventional technique, and can be deposited on the support by spraying or dipping, followed by evaporation of the solvent.

The process of the invention comprises essentially two stages. In a first stage, an electropolymerization is carried out directly on the metallic support or, according to an alternative form, the polymer is prepared in solution and is deposited on the metallic support as indicated above. Then, in a second stage, an oxidation (if the polymer is cationic) or a reduction (if the polymer is anionic) is carried out and, simultaneously, the biologically active substance is attached to the polymer. The oxidation and the reduction, depending on the situation, are carried out electrochemically in a known way by creating a potential difference between the electrically conducting support and the polymer, in order to form respectively positive or negative charges which promote the attachment of the active substance. For example, the formation of a polymer matrix promotes the attachment of an active substance composed of a positively charged phosphorylated nucleic base; conversely, the formation of positive charges in the polymer promotes the attachment of an active substance composed, for example, of an oligonucleotide or a protein carrying negative sites, such as ATP, or more generally any negatively charged particle, such as heparin, a vector for plasmid genes or a linear or circular DNA fragment of plasmid type.

According to a preferred embodiment of the process of deposition of electrically conducting polymer in accordance with the invention, the electrochemical polymerization is carried out in the presence of a water-soluble polymer chosen from a polyethylene glycol, a polyvinylpyrrolidone, a polyethylene oxide, a copolymer of ethylene oxide and of propylene oxide of Poloxamer type, a polyethylene acetate, a poly(vinyl alcohol), a polyacrylamide and water-soluble polyurethane derivatives. The presence of such a water-soluble polymer in the polymer matrix makes it possible to improve the permeability of the polymer to anionic entities, such as oligonucleotides, used as active substance and facilitates the controlled release of these molecules on contact with solutions comprising competing ions originating, for example, from the addition of sodium chloride. Use is preferably made of an amount of polymer representing between 4 and 10% of the overall composition.

More particularly, the polymer film can advantageously be formed in two stages, the first consisting in polymerizing the monomer at a concentration of between 0.01 and 0.1 M approximately, in order to form a bonding layer with a thickness of less than approximately 1 $\mu$m, the second consisting in prolonging the polymerization reaction in the presence of water-soluble polymer, in order to obtain a layer with a thickness of greater than 1 $\mu$m which can be between 2 and 10 $\mu$m approximately.

It is therefore advantageous to use a metallic support made, for example, of steel, of metal alloy or of a metal which is biocompatible and more particularly of stainless steel, tantalum, platinum, gold, nickel-titanium alloy or platinum-indium alloy. A support made of stainless steel can be advantageously used when the electrolytic medium does not comprise chloride. It is also possible to use a nonmetallic support, such as biologically compatible electrically conducting charged polymer.

The oxidation is carried out, after deposition of the polymer as indicated above, by applying an oxidation potential to the support for a predetermined period of time. Thus, for example, depending on the polymer used, it is possible to apply a potential of approximately 0.3V to 1V with respect to a hydrogen reference electrode for a period of time of between 30 minutes and 3 hours approximately, depending upon the properties desired.

According to one characteristic of the invention, by virtue of the oxidation stage, it is possible to adjust the ability of the active substance, in particular oligonucleotides, to attach to the polymer and to subsequently control the release thereof locally on the site to be treated, once the stent has been positioned in the body. The charging of the active substance to the polymer is advantageously carried out simultaneously with the oxidation stage, the concentration of active substance in the oxidation solution being adjusted to an appropriate value which can be between, for example, 1 and 200 $\mu$M, depending on the substance used and the desired degree of attachment. It is thus possible to achieve a degree of attachment of greater than several nanomoles/mg of polymer, in combination with slow release kinetics, ensuring a prolonged effect of the active substance. This technique makes it possible to obtain, for example, release kinetics of the order of several picomoles of active substance per mg of support per day.

The release kinetics observed by using the technique of the invention are related to the thickness of the polymer film. It is possible, in accordance with the invention, to adjust the release kinetics of the active substance by choosing an appropriate thickness of the polymer on the support, for example of between 2 and 10 $\mu$m approximately.

The active substance is chosen according to the use envisaged for the implant. Thus, in the case of a stent covered with a polymer intended for the treatment of post-angioplastic restenosis, the active substance is preferably an antisense oligonucleotide capable of selectively blocking the expression of the genes controlling the proliferation of smooth muscle cells of the arterial wall. Use may be made, for example, of oligonucleotides and more particularly of antisense oligodeoxyribonucleotides (ODN) with a phosphodiester or phosphorothioate structure, which are directed against the insulin-like growth factor receptor (or IGFR) as described by P. Delafontaine et al. ("Regulation of vascular smooth muscle cell Insuline-like Growth Factor I Receptors by phosphorothioate oligonucleotides", J. Biol. Chem., (1995) 270, 14383–388) and WO-A-96.10401, or oligodeoxynucleotides comprising n contiguous guanines, it being possible for n to vary from 2 to 5, as described by Burgess et al. ("The antiproliferative activity of c-myb and c-myc antisense oligonucleotides in smooth muscle cells is caused by a non-antisens mechanism", Proc. Nat. Acad. Sci. USA, (1995) 92, 4051–4055).

These oligodeoxyribonucleotides generally have a very short lifetime in the free state in the body because they are rapidly digested by nucleases, which limits their effectiveness. The present invention is therefore particularly advantageous because it makes it possible to protect these oligodeoxyribonucleotides in the polymer matrix and to deliver them gradually on the same site, where they can then act effectively.

Furthermore, in accordance with the invention, the oligonucleotide can be radioactively labeled. The radioactive isotope makes it possible to monitor the attachment to the polymer and can also result in an antiproliferative effect on smooth muscle cells. The labeling can be carried out conventionally, for example by means of $^{35}$S sulfur or of $^{32}$P phosphorus, the half-lives of which are 87 days and 15 days respectively and are suitable for the development over time of restenosis.

The polymer used for covering the stent, in accordance with the present invention, is chosen from electrically conducting polymers exhibiting satisfactory properties of biological tolerance. Use is preferably made of a polypyrrole, a poly(diaminonaphthalene) or a poly(3,4-ethylenedioxythiophene) or poly(EDT), which exhibit appropriate electrical conduction and mechanical strength properties without harming the mechanical qualities of the support used.

It can be advantageous, in accordance with the present invention, to apply, to the polymer carrying the oligonucleotide, a layer of substance, such as fibrin, known for its antithrombotic activity.

The invention applies very particularly to a stent covered with a polymer comprising an active substance which is effective in the treatment of restenosis. It can apply more generally to any implant capable of being covered with a layer of cationic (or cationizable) or anionic (or anionizable) polymer which can act as reservoir of active substance carrying positive or negative charges which is intended to be released locally, for example substances exhibiting pharmacological properties of use in the treatment of leukemias, solid tumors and organ rejections.

The examples below illustrate the invention in more detail without limiting the scope thereof.

EXAMPLE 1

The electropolymerization of 3,4-ethylenedioxythiophene is carried out by means of a conventional electrochemical cell comprising three electrodes: a platinum counterelectrode, a silver wire covered with silver chloride acting as reference electrode providing a constant potential, and a working electrode of platinum sprayed onto a glass plate with an area of 0.6 cm², giving a potential with respect to the counterelectrode.

The vessel of the cell comprises the solution of monomer to be polymerized and the salt providing the electrical conduction.

The monomer is 3,4-ethylenedioxythiophene, to which a polyethylene glycol ($3 \times 10^{-2}$ M) or a polyvinylpyrrolidone ($2 \times 10^{-3}$ M) is added. The electrolytic solution is PBS (phosphate buffered saline) at pH 7.4 comprising the following salts: KCl (2.7 mM), NaCl (0.14 M), $KH_2PO_4$ (1.4 mM) and $Na_2HPO_4$ (6.4 mM).

The monomer is added to the PBS solution diluted 15 fold. The potentiodynamic method (cyclic voltametry) is used, the potential ranging from −0.1V to +1.3V with respect to Ag/AgCl for 10 to 30 cycles. Oxidation of the monomer begins at approximately 0.9V. The final cycle is halted at the higher potential in order to obtain a homogeneous oxidized film. The thickness of the film, measured by means of a scanning electron microscope, is 2.5 $\mu$m (10 cycles) or 5.4 $\mu$m (20 cycles). The thickness of the film can be increased by increasing the number of cycles. However, beyond approximately 30 cycles, there is a risk of the mechanical properties of the film deteriorating.

One of the oligonucleotides indicated below is subsequently incorporated as active substance by oxidizing the polymer at a potential of +0.7V with respect to an Ag/AgCl reference electrode in a PBS solution comprising an amount of oligonucleotide equal to 1 $\mu$M. The potential is maintained for approximately 1 h 30.

The polymer film charged with oligonucleotide is quickly rinsed with water on both faces of the working electrode.

The antisense oligodeoxyribonucleotides (ODN) successively used in this example are as follows:

5'-CTC-TCG-CAC-CCA-TCT-CTC-TCC-TTC-T (phosphorothioate)

IGFR TCC-GGA-GCC-AGA-CTT-CAT-TC (phosphorothioate)

C-Myc 5'-AAC-GTT-GAG-GGG-CAT (phosphodiester).

These ODN are purified by high performance liquid chromatography (HPLC) on a reversed-phase C18 column using tetraethylammonium acetate/acetonitrile elution buffers.

In order to monitor the encapsulation of the oligodeoxyribonucleotides (ODN) in the polymer film, radioactive labeling is carried out according to a conventional technique using $^{32}P$ as isotopic label.

The labeling is carried out by transfer of a $^{32}P$ radioactive phosphate group from ATP to the 5' position of the ODN by polynucleotide kinase at 37° C. in acetate buffer medium.

EXAMPLE 2

The electropolymerization is carried out of a naphthalene derivative, 5amino-1,4-naphthoquinone (ANQ, concentration $10^{-2}$ M), in an acetonitrile solution comprising $10^{-1}$ M $LiClO_4$. The potentiodynamic method (cyclic voltametry) is used, the potential being varied from 0.5V to 1.45V with respect to a calomel reference electrode (SCE) for 40 minutes.

The thickness of the film, measured by means of a scanning electron microscope, is 1 $\mu$m.

The positively charged active substance is subsequently incorporated by reducing the polymer at a potential of −0.3V with respect to an SCE in an aqueous solution with a pH of approximately 7 comprising the positively charged substance. The potential is maintained for approximately 20 minutes.

EXAMPLE 3

The procedure is as in Example 1,3,4-ethylenedioxythiophene being used as monomer but the polymer film being formed in two successive stages.

In a first stage, the monomer is polymerized in the same PBS medium as in Example 1 diluted 15 fold. The concentration of monomer is $3 \times 10^{-2}$ M. The technique used is identical to that of Example 1 but with only two scanning cycles being carried out, so as to form a film with a thickness of approximately 0.5 $\mu$m constituting a bonding layer.

In a second stage, a polyvinylpyrrolidone with a molar mass of approximately 40,000 is added to the medium at a concentration of $2 \times 10^{-3}$ M and the polymerization is prolonged until a poly(3,4-ethylenedioxythiophene) film exhibiting a thickness of approximately 6 $\mu$m is obtained.

The tests carried out using a platinum stent as support have demonstrated the excellent mechanical properties of the polymer coating, which has good adhesion.

EXAMPLE 4

The experiments carried out with the stents of the invention have demonstrated very good tolerance after implantation in vivo, allowing their use to be envisaged in the treatment of restenosis.

Thus, a platinum stent covered with polymer prepared as indicated in Example 1, which stent has a mesh structure, was implanted in the abdominal aorta of two New Zealand rabbits weighing 3.5 kg. An identical stent but not covered with polymer was implanted in the same animal, in the same aorta but 2 cm upstream, and acts as control stent. Treatment with aspirin was begun one day before the operation (0.07 mg/ml of drinking water) and then prolonged throughout the duration of the implantation. The two arteries were removed three and fifteen days after inserting the stent and examined by standard histology after fixing.

On the 3rd day, parietal thrombus is not observed. A moderate proliferation, not covering the meshes of the stent, of smooth muscle cells is recorded at the contact regions between the stent and the arterial wall. The presence of some circulating erythrocyte and polynuclear cells and of some collagen fibers is recorded. The appearance of the two stents, that is to say the control stent and the stent covered with polymer, is identical.

On the 15th day, no parietal thrombus is observed. The proliferation of the smooth muscle cells is somewhat more accentuated and is composed of the same components as above. The proliferative layer is more organized, covers the meshes of the stent covered with polymer and exhibits a layer of endothelial cells at the surface, thus promoting the stabilization of the process.

These tests confirm the properties of bio- and hemocompatibility of the poly(EDT) polymer used in accordance with the invention.

What is claimed is:

1. Device which can be implanted in the body, which comprises an electrically conducting support covered with a layer of electrically conducting polymer, to which layer is attached at least one biologically active substance of an anionic or cationic nature.

2. Device according to claim 1, characterized in that the polymer is a polymer derived from pyrrole, naphthalene or thiophene.

3. Device according to claim 2, characterized in that the polymer is a poly(3,4-ethyienedioxythiophene).

4. Device according to claim 3, characterized in that the biologically active substance is a phosphorylated nucleic base, an antisense oligonucleotide or a vector for plasmid genes.

5. Device according to claim 3, characterized in that the electrically conducting support is a metal chosen from a stainless steel, tantalum, platinum, gold, a nickel-titanium alloy or a platinum-indium alloy.

6. Device according to claim 2, characterized in that the biologically active substance is a phosphorylated nucleic base, an antisense oligonucleotide or a vector for plasmid genes.

7. Device according to claim 2, characterized in that the electrically conducting support is a metal chosen from a stainless steel, tantalum, platinum, gold, a nickel-titanium alloy or a platinum-indium alloy.

8. Device according to claim 1, characterized in that the biologically active substance is a phosphorylated nucleic base, an antisense oligonucleotide or a vector for plasmid genes.

9. Device according to claim 8, characterized in that the biologically active substance is an antisense oligodeoxyribonucleotide (ODN) comprising a phosphodiester or phosphorothioate structure.

10. Device according to claim 1, characterized in that the electrically conducting support is a metal chosen from a stainless steel, tantalum, platinum, gold, a nickel-titanium alloy or a platinum-indium alloy.

11. Device according to claim 1, characterized in that it is composed of a stent.

12. Process for the deposition of a polymer on an electrically conducting support for a device which can be implanted in the body according to claim 1, comprising, in a first stage, carrying out an electropolymerization directly on a metallic or non-metallic support or, according to an alternative form, the polymer is prepared in solution and is deposited on the support and then, in a second stage, an oxidation or a reduction is carried out and the biologically active substance with an anionic or cationic nature is attached to the polymer.

13. Process according to claim 12, characterized in that the electropolymerization is carried out in the presence of a water-soluble polymer.

14. Process according to claim 13, characterized in that the water-soluble polymer is chosen from a polyethylene glycol, a polyvinylpyrrolidone, a polyethylene oxide, a copolymer of ethylene oxide and of propylene oxide of Poloxamer type, a polyethylene acetate, a poly(vinyl alcohol), a polyacrylamide and water-soluble polyurethane derivatives.

15. Process according to claim 14, characterized in that the charging of the active substance to the polymer is carried out simultaneously with the oxidation or reduction stage.

16. Process according to claim 13, characterized in that the charging of the active substance to the polymer is carried out simultaneously with the oxidation or reduction stage.

17. Process according to claim 12, characterized in that the oxidation is carried out electrochemically.

18. Process according to claim 17, characterized in that the charging of the active substance to the polymer is carried out simultaneously with the oxidation or reduction stage.

19. Process according to claims 8 to 12, characterized in that the charging of the active substance to the polymer is carried out simultaneously with the oxidation or reduction stage.

20. Process according to claim 12, wherein the electrically conducting support is a metal chosen from a stainless steel, tantalum, platinum, gold, a nickel-titanium alloy or a platinum-indium alloy.

* * * * *